Figure 1:
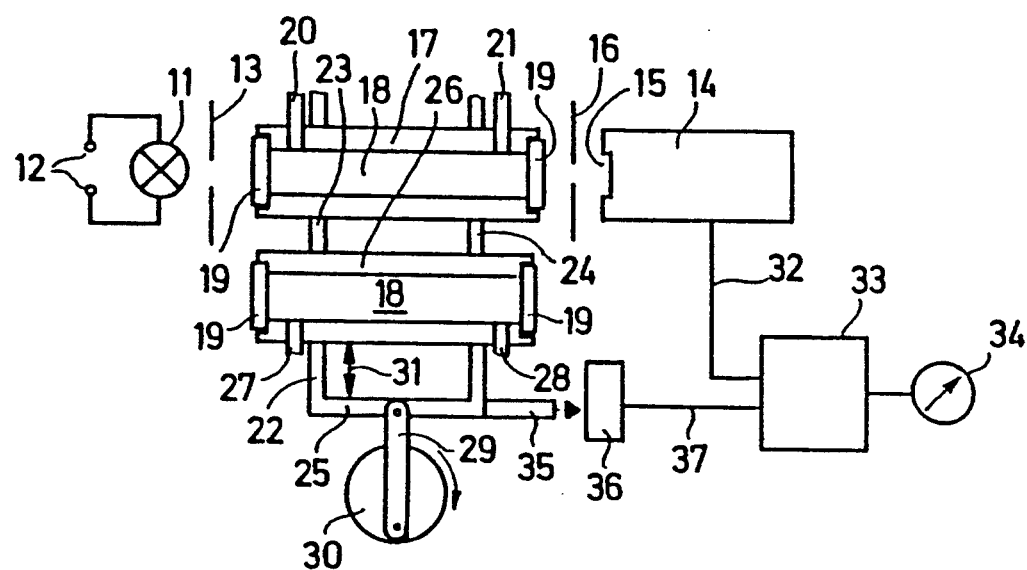

United States Patent [19]

Nonnenmacher

[11] Patent Number: 5,334,536
[45] Date of Patent: Aug. 2, 1994

[54] APPARATUS FOR THE PHOTOMETRIC DETERMINATION OF GAS CONCENTRATIONS

[76] Inventor: Klaus Nonnenmacher, Dischingerweg 11, D-7400 Tuebingen 5, Fed. Rep. of Germany

[21] Appl. No.: 898,220

[22] Filed: Jun. 12, 1992

[30] Foreign Application Priority Data

Jun. 12, 1991 [DE] Fed. Rep. of Germany ....... 4119346

[51] Int. Cl.$^5$ ............................................. G01N 21/00
[52] U.S. Cl. .................................. 436/135; 422/239; 422/68.1; 422/83; 422/82.05
[58] Field of Search ............... 422/239, 212, 111, 129, 422/168, 68.1, 69, 82.05, 83; 261/94; 356/51, 93, 206; 73/1901–1907; 436/135

[56] References Cited

U.S. PATENT DOCUMENTS

| | | | |
|---|---|---|---|
| 2,088,497 | 7/1937 | Tijmstia | 261/94 |
| 2,165,489 | 6/1939 | Kranz | 261/94 |
| 3,193,360 | 7/1965 | Scoggin | 261/94 |
| 3,466,149 | 9/1969 | Blood et al. | 261/94 |
| 3,788,070 | 1/1974 | Camarasa et al. | 422/168 |
| 3,796,657 | 3/1974 | Pretorious et al. | 261/94 |
| 3,897,153 | 7/1975 | Keenan et al. | 356/51 |
| 4,065,412 | 12/1977 | Dreyer | 422/129 |
| 4,704,256 | 11/1987 | Hood et al. | 422/116 |
| 4,765,280 | 8/1988 | Kobayashi et al. | 261/94 |
| 4,916,079 | 4/1990 | Baillie et al. | 422/68.1 |
| 5,064,506 | 11/1991 | Sparenberg et al. | 261/148 |
| 5,120,403 | 6/1992 | Smith, Jr. | 422/111 |

FOREIGN PATENT DOCUMENTS 615964 1/1961 Italy.

*Primary Examiner*—Robert J. Warden
*Assistant Examiner*—E. Leigh Dawson
*Attorney, Agent, or Firm*—Quarles & Brady

[57] ABSTRACT

A process and apparatus for measuring the concentration of gases in a medium are provided in which the radiation absorption of the gas in the medium is determined with the aid of a sample measurement and reference measurement. The medium with the gas is continuously passed through a measuring cell, and a reference medium not containing the measured gas is continuously passed through a reference cell. Both cells are alternately brought into the optical path between a lamp and a photoreceiver. The results of the absorption measurement in the measuring cell and the reference cell are divided. The concentration of a gas in a liquid, or ozone in water, can be measured by passing the liquid through an exchange material in a packed tower, through which a reference gas stream is passed in counterflow manner. An exchange of the measured gas occurs from the liquid stream to the reference gas stream. The absorption of the measured gas in the reference gas stream is determined alternately with the absorption of a stream of the reference gas without any measured gas, from which the concentration of the measured gas in the liquid medium is calculated. A packed column with a pressure compensating line may be provided to prevent flooding of the column and to ensure continuous operation of the exchange material.

6 Claims, 5 Drawing Sheets

APPARATUS FOR THE PHOTOMETRIC DETERMINATION OF GAS CONCENTRATIONS

The invention relates to a process for determining the concentration of gases, particularly ozone, in which with the aid of a photometer the radiation absorption of the gas is measured and compared with a reference absorption, as well as to an apparatus for performing the process.

It is known to determine the concentration of gases by measuring the absorption of a radiation, the absorption of the particular gas being measured in comparison with a reference medium, which does not contain the gas to be measured. For example, the concentration of ozone is measured by absorption in the UV-range. It has already been proposed to place in the optical path of a UV-photometer a measuring cuvette or cell, in which with the aid of valves alternately the gas or liquid to be measured is brought into contact with the ozone and the same medium without ozone. Conclusions can be drawn on the ozone concentration from the comparison of both measurements. However, it has been found that in the case of mechanical devices, namely valves, due to the simultaneously occurring mechanical and chemical stressing by the constant opening and closing of the valves and the action of the aggressive ozone the durability of the valves is greatly reduced. It has also been found that the intensity of the discharge lamps used as a radiation source is subject to both time and spatial fluctuations, which do not allow adequately accurate results to be obtained for the existing precision requirements.

The problem of the invention is to provide a process of the aforementioned type, which can be performed very simply and which supplies very accurate measurements also in continuous operation. The apparatus for performing the process must also have a very simple construction and must be suitable for permanent operation and the result supplied must be very accurate.

According to the invention this problem is solved by a process of the aforementioned type, in which the medium to be investigated and the medium used for the reference measurement are in each case passed into a single cell and the two cells are alternately brought into the optical path of the photometer. Due to the fact that the two cells are alternately brought into the same optical path, the effects of local fluctuations in the intensity of the radiation source are eliminated. Through the use of in each case one measuring cell and a reference cell the process can be used continuously, without requiring complicated, fault-prone valves.

The introduction of the cells into the optical path can take place by moving the cells with the radiation source and photoreceiver fixed, and by moving the radiation source and photoreceiver with the cells fixed. It is naturally also possible to move the radiation source and the cells.

For producing a suitable reference medium the invention proposes removing from the medium to be investigated by means of a chemical reaction the gas, whose concentration is to be measured and then using as the reference medium the medium which has been freed from the gas.

For performing the chemical reaction a gas, which performs a reaction with the corresponding gas, is supplied via a diaphragm. As during the measurement very low flow rates are used, the gas to be supplied must also be introduced at a very low speed. However, this is not possible when using valves. However, when using a diaphragm a very low inflow speed can be achieved, which can be kept within narrow limits by maintaining the pressure constant.

If the gas, whose concentration is to be determined, is ozone, the invention proposes using NO as the gas to be introduced.

The invention also proposes that the measured values of the radiation absorption be divided. As a result of the conventionally used difference method the advantage occurs that influences, such as e.g. through further absorbing components in the medium to be investigated, cell dirtying, organic substances, etc. lead to a falsification of the measured results. In the quotient method, in which the results of the absorption measurement of the measuring cell and the reference cell are divided, the influence of these quantities is eliminated.

As a further development of the process the invention proposes that the cells are fixed and the radiation source is moved and in particular rotated. This process is particularly appropriate at higher concentrations.

However, as is also proposed by the invention, it is also possible to move the cells in preferred manner transversely to the radiation direction. This embodiment of the inventive process is advantageously used in the case of low concentrations.

The invention also proposes an apparatus for determining the concentration of gases, particularly ozone, with a radiation source, at least one photoreceiver and at least one cell which can be brought into the optical path, in which according to the invention a measuring cell containing the medium with the gas to be determined and an optically identical reference cell containing a reference medium are alternately movable into the optical path.

Due to the fact that the same optical path is used for the measuring cell and the reference cell, local fluctuations in the intensity of the radiation source have no influence on the measured result. The time fluctuations of the intensity can be eliminated with respect to their influence on the measured result in that the alternate movement of the two cells takes place more rapidly than the fluctuations of the light intensity, which is approximately one minute. The movement of the two cells relative to the radiation source can be a rotary, pivoting or sliding movement.

According to a further development, for the continuous monitoring of the concentration of a particular gas, the gas continuously flows through the measuring cell.

Advantageously, according to a further development, a reaction chamber is positioned downstream of the measuring cell and is connected by means of a line to said measuring cell and to the reference cell. The medium with the gas to be measured consequently firstly flows through the measuring cell into the reaction chamber and from the latter through the reference cell. The reaction chamber contains an inlet for a gas, which performs a reaction with the gas to be measured, which eliminates the gas to be measured. Thus, in very simple manner a reference medium is obtained and it is also ensured that the gas, whose concentration is to be determined and which is possibly harmful, is also eliminated without additional costs.

To permit a very limited inflow speed of the gas to be supplied, according to the invention the inlet is separated by a diaphragm from the reaction chamber. This permits very low, but constant inflow speeds.

According to a further development of the invention a suction pump is positioned downstream of the reaction chamber.

According to a further development of the invention a mechanical drive alternately moves the two cells into the optical path of the fixed radiation source. This construction of the apparatus is particularly advantageous if there are low concentrations of the gas to be measured.

According to another development of the invention a mechanical drive moves the photoreceiver and the radiation source at right angles to the fixed cells. This is particularly suitable for high concentrations of the gas to be investigated.

As is also proposed by the invention, it is also possible for the radiation source to be driven in rotary manner and during the rotation the radiation direction alternately coincides with the measuring cell and the reference cell. For example, the two cells can be displaced by 180° relative to the rotation axis of the radiation source and there are two photoreceivers. However, it is also possible to parallel juxtapose the cells and for the radiation source to radiate by means of a mirror arrangement alternately into the two cells and once again two photoreceivers can be present. It is naturally also possible to recombine the path of the beam following the cells by means of prisms, mirrors, etc., so that only one photoreceiver is used.

To clearly indicate the evaluation electronics of the inventive apparatus, which divides the two measured values, when it performs a measurement of either the measuring cell or the reference cell, the invention also proposes that a positioning device is provided for controlling an evaluating circuit associated with the photoreceiver. This positioning device e.g. always supplies a signal, if the measuring cell is in the optical path of the photometer.

A particularly favourable embodiment of the invention is provided if a mechanically driven slide linearly displaces the two cells.

The process and apparatus proposed by the invention can be used both for measuring the concentration of gas in gas and also gas in liquid. In this case, to make available the reference medium, the gas to be investigated must be selectively removed from the liquid, which can in certain cases lead to problems. When determining ozone in water, e.g. the ozone must be selectively removed without modifying the organically caused extinction of the water. The photometry can also be harmed by gas bubble absorption on the cell windows or walls and by the formation of layers and coatings. Thus, the process proposed by the invention is so performed when measuring the concentration of gas in liquid, particularly ozone in water, that the water with the ozone is initially passed through a contact apparatus, namely a so-called packed column, through which an air flow takes place in the opposite direction. Part of the ozone dissolved in the water is passed into the air flow. It has been found that under certain operating conditions the concentration of the gas in air is proportional to the concentration of the gas in liquid. When operating an inventive apparatus in this operating range it is possible to carry out a continuous measurement of the concentration of zone in water. It has found that the maintaining of this operating range is critical. In the case of minor vibrations, impacts or irregularities in the water feed, the packed column can be flooded and is consequently made impermeable for the through-flow of air. If this occurs the operator must take action in order to allow the continuation of the process. In order to be able to continuously perform the inventive process using the inventive apparatus with a contact device without supervision, the invention proposes a packed column with an upper storage container for the liquid, a central intermixing part connected thereto by means of an outlet from the storage container and which contains the packing and the air outlet, as well as a lower part with an air inlet and the liquid outlet, the intermixing part being connected by means of a pressure compensating line to the storage container. This measure makes the flooding of the packed column impossible.

According to a further development, above the support tray connecting the intermixing part to the lower part is provided a lifting tray carrying the packing. This measure also assists the continuous, faultless operation.

According to a further development the mouth of the pressure compensating line is located in the intermixing part above the packing and in the storage container above the maximum liquid level.

Further features, details and advantages of the invention can be gathered from the following description of preferred embodiments of the invention, together with the attached drawings, wherein show:

FIG. 1 A diagrammatic view of an inventive apparatus.

Figure 2:
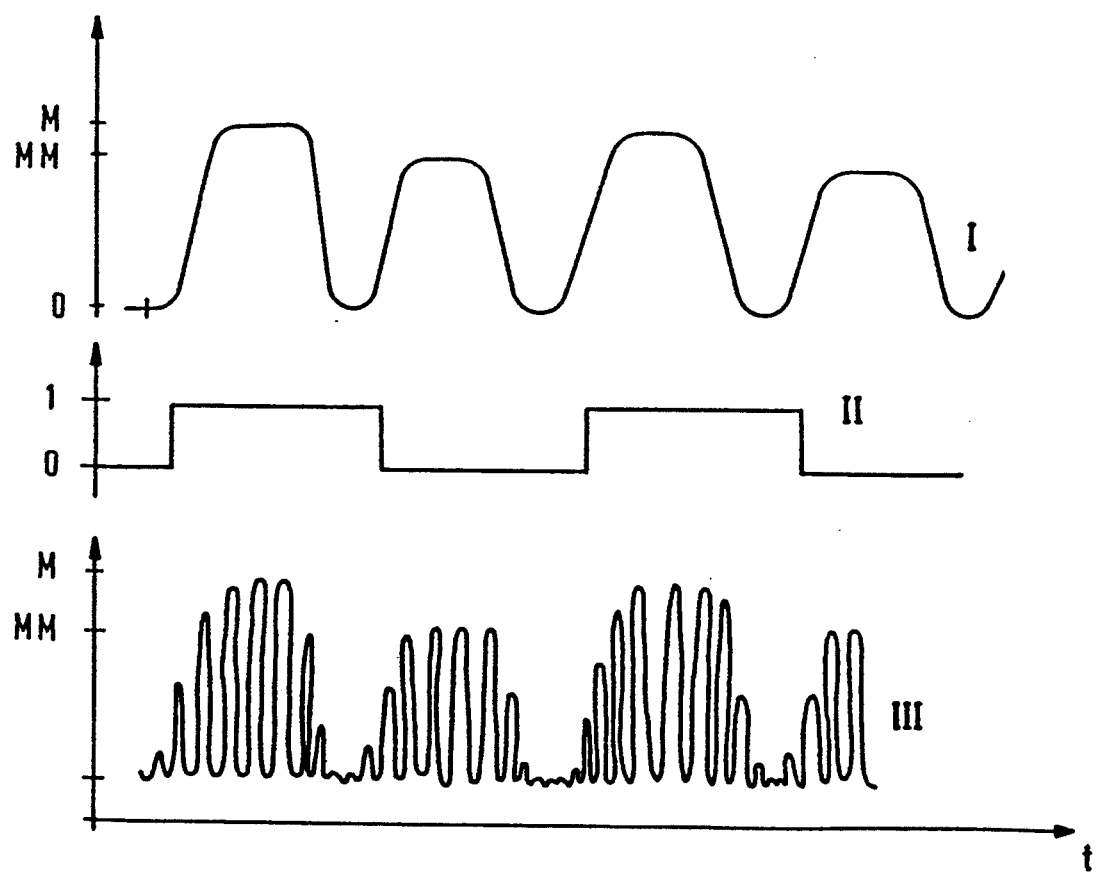

FIG. 2 Measured signals occurring with the apparatus of FIG. 1.

Figure 3:
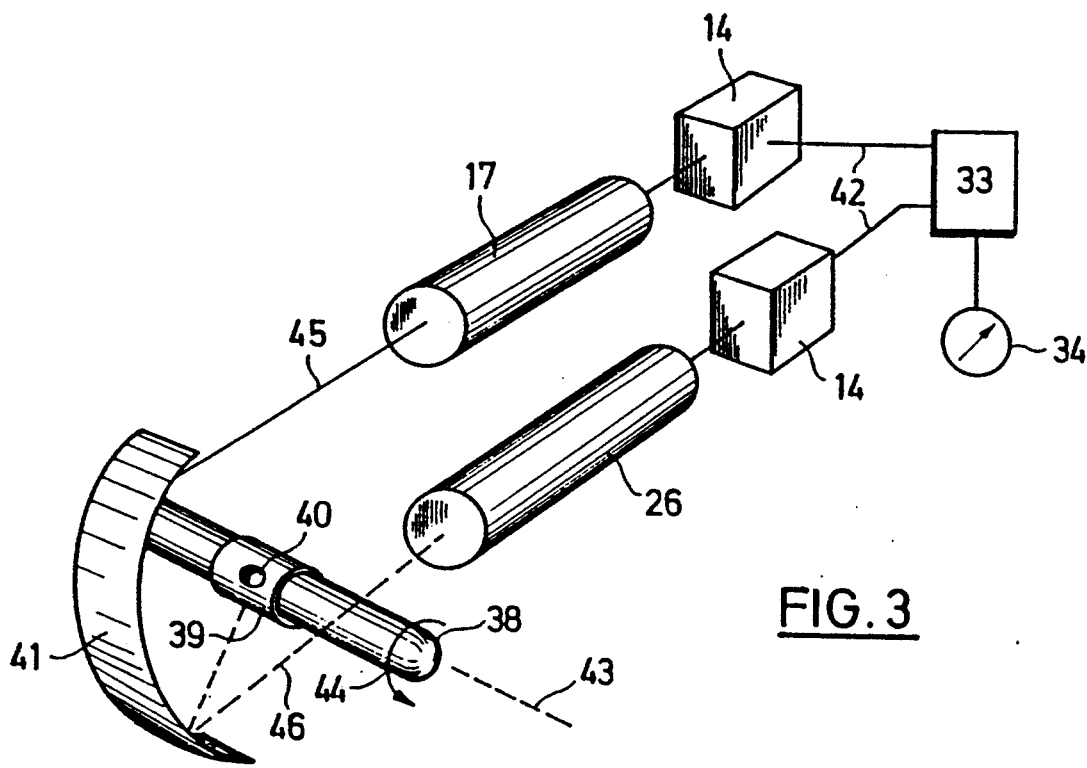

FIG. 3 A diagrammatic view of a second embodiment of the invention.

Figure 4:
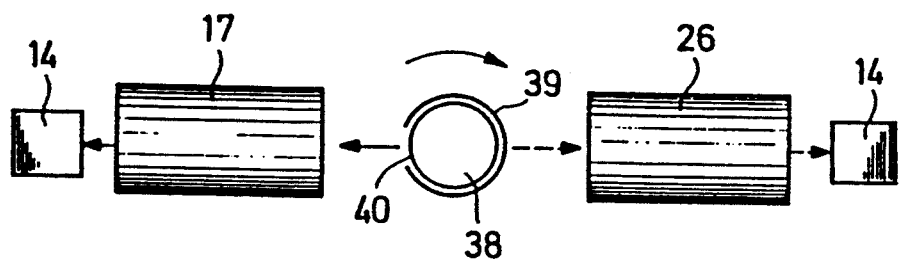

FIG. 4 A diagrammatic plan view of a third embodiment.

Figure 5:
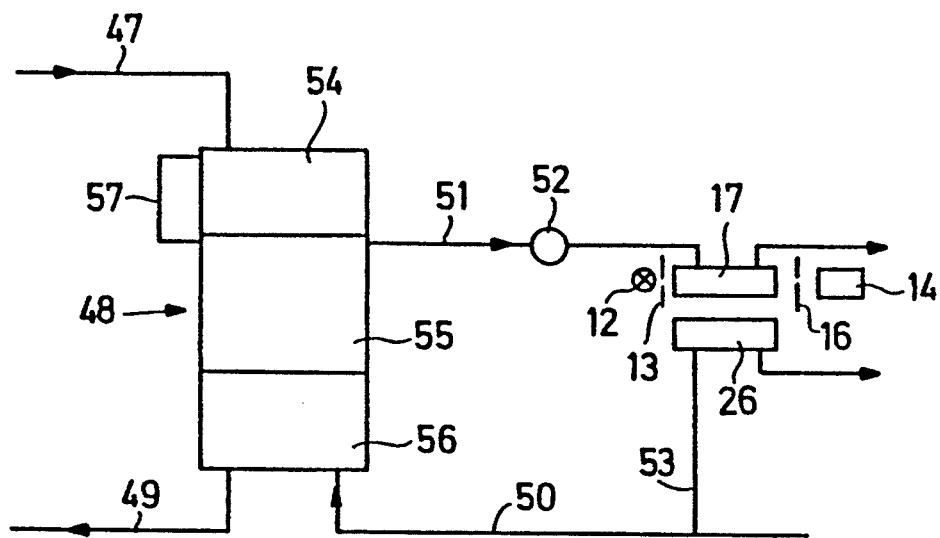

FIG. 5 A highly simplified representation of a further embodiment.

Figure 6:
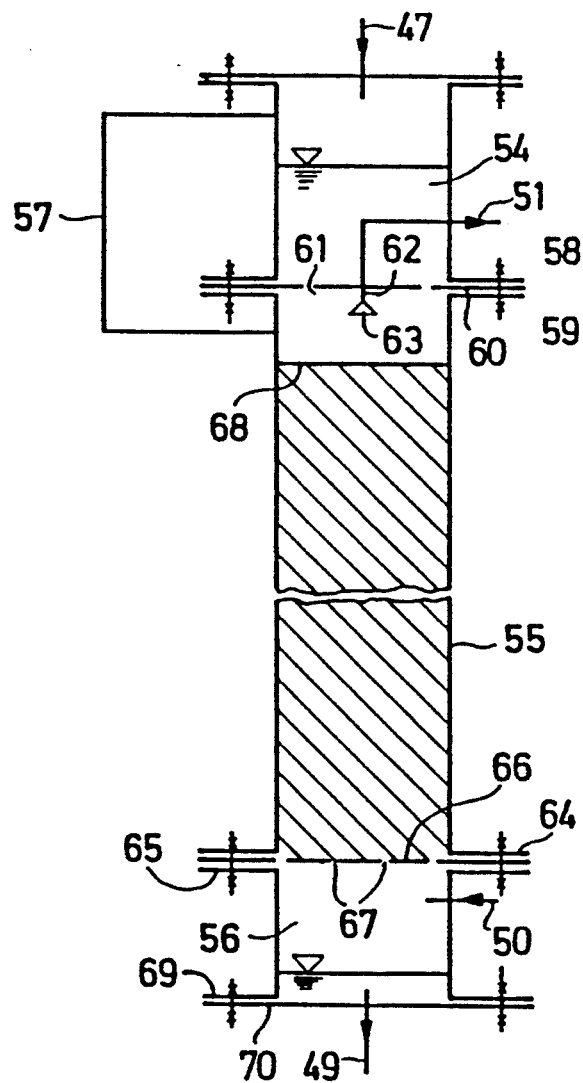
Figure 7:
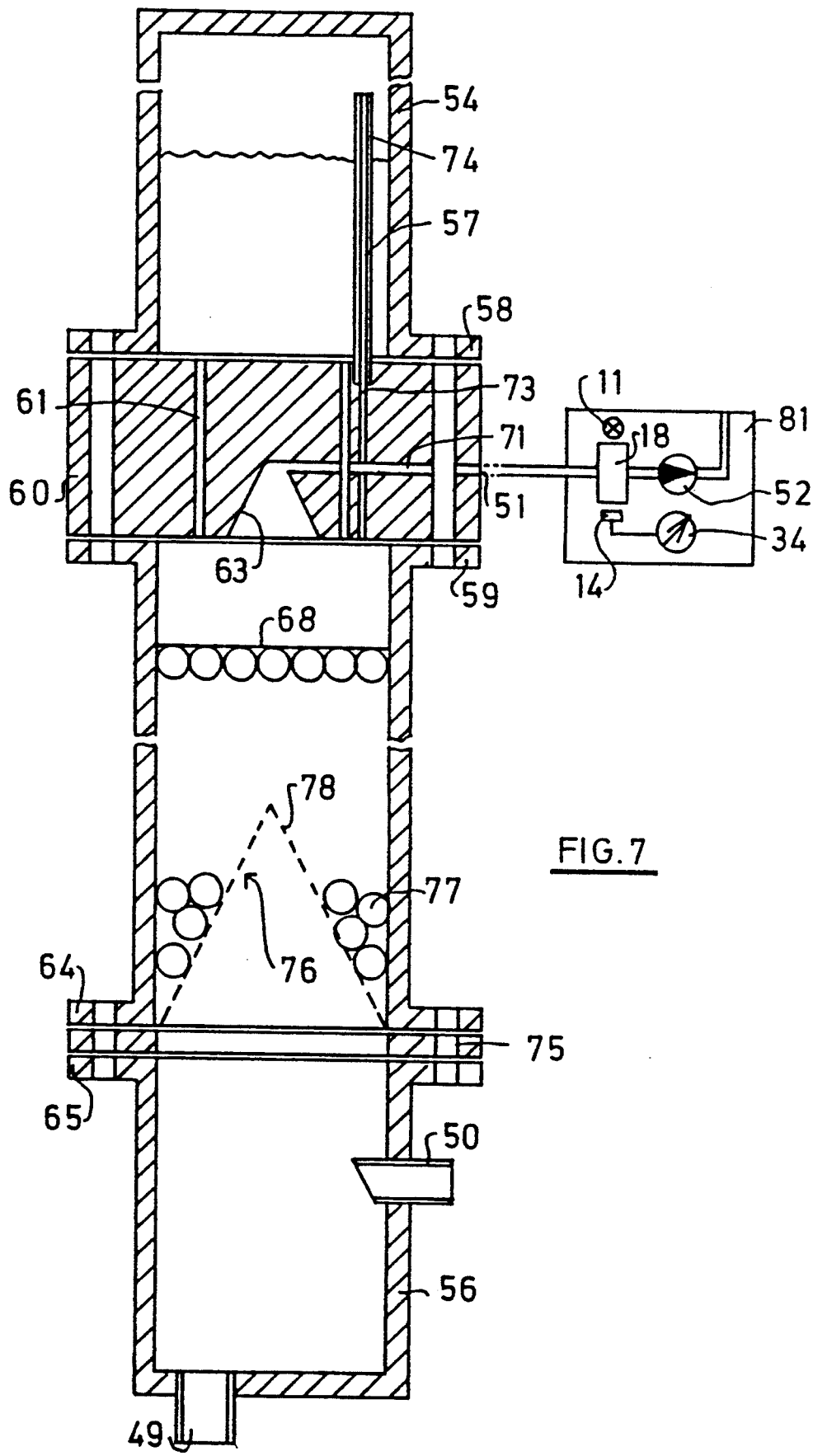

FIGS. 6 & 7 A packed column used in conjunction with the inventive process.

Figure 8:
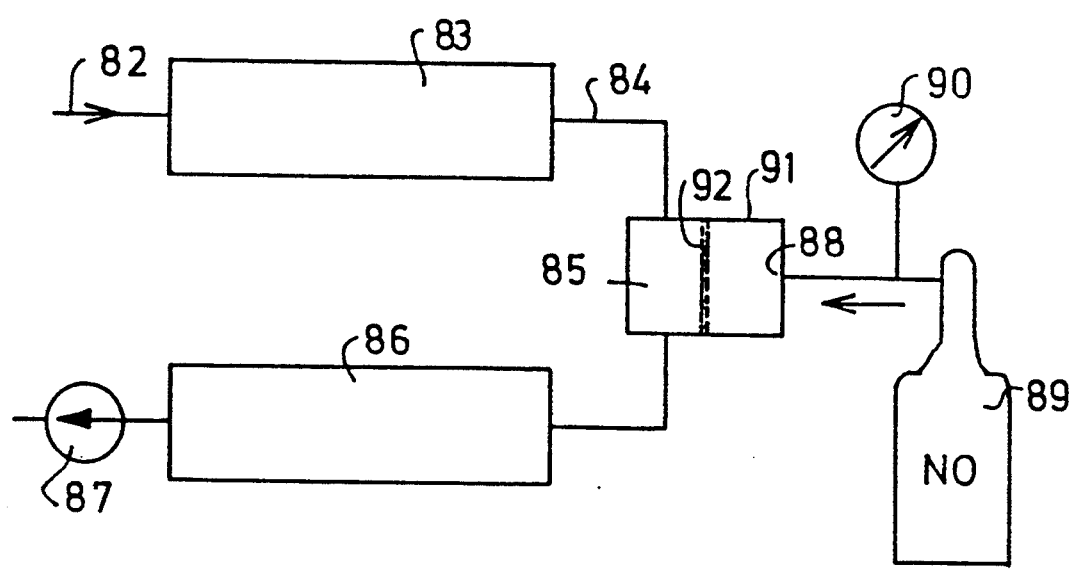

FIG. 8 Diagrammatically a possibility of preparing a reference gas.

In the arrangement according to FIG. 1 it is possible to see to the left the radiation source in the form of a lamp 11, which is operated with alternating or direct current at the terminals 12. To the right of the lamp 11 is provided a diaphragm 13, which defines the radiation direction of said lamp. In a linear extension on the right-hand side is provided a photoreceiver 14, upstream of whose photosensitive intake 15 is provided a diaphragm 16. In the optical path between the lamp 11 and the photoreceiver 14 there is a measuring cell 17 having a cylindrical bore 18. On both sides the bore 18 is closed with the aid of a quartz glass cover 19, quartz glass being used in the present case because it is permeable to the ultraviolet radiation used in the ozone measurement. When measuring in another frequency range a corresponding glass would be used.

The measuring cell 17 has an inlet 20 and an outlet 21, which are connected to hose lines, through which continuously flows the medium to be investigated, e.g. air, with a proportion of ozone.

The measuring cell 17 is mounted on a slide 22, which has two arms 23, 24, which are interconnected by a bar 25 on their side remote from the cell 17. Parallel to the measuring cell 17 an optically identical reference cell 26 is fixed to the slide 22 and also has two quartz glass covers 19 and a cylindrical bore 18. Into the reference cell 26 passes an inlet 27 and an outlet 28 for the reference medium, e.g. air, from which the ozone has been removed. The reference cell 26 has the same length, diameter and thickness of cover 19 as the measuring cell 17.

In the centre of the bar 25 is articulated a connecting rod 29, whose other end is articulated in the vicinity of the circumference of a crank disk 30, which is driven in rotary manner by a mechanical drive. The rotation of the crank disk 30 leads to a displacement of the slide 22 in the direction of the double arrow 31. The guide for the slide 22 is not shown for reasons of simplification. It can be seen that in FIG. 1 the bottom dead centre of the movement of the slide 22 is shown. The length of the connecting rod 29 and the dimensions of the crank disk 30 are selected in such a way that in the top dead centre of the slide 22 the reference cell 26 precisely assumes the position assumed by the measuring cell 17 in FIG. 1, i.e. is located in the optical path between the lamp 11 and the photoreceiver 14.

The photoreceiver 14 is connected with the aid of a line 32 to an evaluation logic 33, which carries out a division of the measured results of the absorption in the measuring cell 17 and in the reference cell 26. To the evaluation logic 33 is connected a measuring instrument 34, which directly indicates the gas concentration.

The bar 25 of the slide 22 has an attachment 35, which cooperates with a positioning device 36. This is only diagrammatically represented in the drawing, the signals of the positioning device being shown in detail in FIG. 2. FIG. 2 is the curve I of the output signals of the photoreceiver 14 on the line 32, if a d.c. voltage is applied to the terminals 12 of the lamp 11. The abscissa in FIG. 2 represents the time, whilst the ordinates e.g. represent the voltage values. It is apparent from the curve I, that starting from the value zero the voltage on the line 32 initially rises, namely if the reference cell 26 is moved into the optical path, where the output signal of the photoreceiver 14 reaches a maximum M. The maximum is maintained for as long as the reference cell 26 is in the optical path. The reference cell is then removed again from the optical path and in the area between the two cells the output value of the photoreceiver 14 drops to zero. The measuring cell 17 then passes into the optical path, so that the output of the photoreceiver 14 again assumes a relative maximum MM which, compared with the maximum M, represents the radiation absorption of the gas to be investigated, so that from the difference or ratio of M to MM conclusions can be drawn regarding the gas concentration. FIG. 2 shows that the maxima M and relative maxima MM constantly alternate, the frequency of the maxima being determined by the rotation speed of the crank disk 30. The evaluation logic 33 in FIG. 1 now determines the quotient from a maximum M and the adjacent relative maximum MM and from this conclusions can be drawn regarding the concentration of the gas to be investigated. This division is redetermined for each new maximum of the curve I, so that the intensity fluctuations of the lamp 11 can have no effect for as long as only the frequency of the maxima of curve I, i.e. the rotary movement of the crank disk 30, is greater than the frequency of the fluctuations, which are in the minute range.

To indicate to the evaluating circuit 33 whether it receives on the line 32 a maximum M or a relative maximum MM the positioning device 36, on which acts the attachment 55, supplies a signal via the line 37 and its time pattern is represented by the curve II in FIG. 2. Whenever the reference cell 26 passes into the optical path, the positioning device 36 supplies a signal of amplitude 1, whereas if the measuring cell is in the optical path, a signal zero is supplied.

Curve III in FIG. 2 represents the signals on the line 32, if a.c. voltage is applied to the terminals 12 of the lamp 11. The curve I represents the envelope of the curve III.

The process according to the invention is performed in the following way with the aid of the apparatus according to FIG. 1. Through the cell 17 flows the medium with the gas to be investigated, e.g. air and with an ozone proportion to be measured. Through the reference cell 26 flows the same air, but from which the ozone has been selectively removed. Both flows are continuous. The crank disk 30 is rotated, so that alternately the reference cell 26 and the measuring cell 17 pass into the optical path and from the curves I or III the maxima and the relative maxima are determined and interlinked by means of a division. The evaluating circuit 33 then calculates therefrom the particular ozone concentration in the air. The measured result is indicated on the measuring instrument 34.

FIG. 3 shows another embodiment of an inventive apparatus for performing the inventive process. In this case the lamp 38 is surrounded by a sleeve 39, which has one or more openings 40. On the left-hand side of the lamp 38 in FIG. 3 is located a concave mirror 41, which reflects the light beams from the opening 40 of the sleeve 39 in the direction of the cells 17 and 26. On the far side of the cells 17 and 26 are provided two photoreceivers 14, 14', whose outputs are connected to the evaluation logic 33 by means of two lines 42. For reasons of simplicity the cells 17, 26 are only diagrammatically shown, but correspond to cells 17, 26 in FIG. 1.

The lamp 38 is rotatable about the broken-line axis 43, rotation taking place in the direction of the arrow 44. For current transmission purposes slip rings or the like can be provided in per se known manner. The sleeve applied to the lamp 38 ensures that only a single beam or beam bundle can pass out of the opening 40. Obviously several openings can be provided. On rotating the lamp 38 in the direction of the arrow 44 the lamp initially passes into the position shown in FIG. 3, in which the ultraviolet beam passing out of the opening 40 passes in the direction of the light path 45 through the measuring cell 17 onto the photoreceiver 14. Thus, at this time an absorption measurement takes place, which is further processed in the evaluation logic 33. On further rotating the lamp 38 in the direction of the arrow 44 the sleeve 40 finally comes into a position in which the light path passes along the broken line 46. The ultraviolet light now passes through the reference cell 26 onto the second photoreceiver 14 and the absorption is now measured without the gas to be investigated. In the evaluation logic 33 there is once again a division of the two maximum values and the measuring instrument 34 indicates the ozone concentration.

In the arrangement shown in FIG. 3 prisms or mirrors could be connected e.g. to the cells 17, 26 and which make the optical beam converge onto a single photoreceiver 14.

FIG. 4 shows an arrangement in which the lamp 38 is again arranged in rotary manner and on this occasion the two cells 17, 26 are located on a line passing through the rotation axis of the lamp 38. The embodiment of FIG. 4 can be modified in such a way that the cells rotate or pivot about the stationary lamp 38.

FIG. 5 diagrammatically shows the process according to the invention, if it is a question of very accurately measuring the concentration of a gas in a liquid. This process is used with particular advantage for measuring the ozone concentration in water. The ozone-containing water passes via the inlet line 47 into a packed column 48 from which it passes out again by means of the outlet line 49. An air flow passes in the opposite direction through the packed column 48, entering the said column by the inlet line 50 and passing out of it through the outlet line 51. In this example a pump 52 is provided in the outlet line 51. From the pump 52 the air is passed into the measuring cell 17 of an apparatus according to the invention and then passes out of it again. The air sucked through the inlet passes via a branch line 53 into the reference cell 26 of the measuring apparatus.

The packed column 48 comprises an upper storage container 54, through which the water passes through openings into the central intermixing part 55, which contains packings. The lower part 56 of the packing column 48 serves to remove the water from or introduce the air into said column. The upper part of the intermixing part 55 is connected by means of a return line 56 to the storage container 54. Details of the packed column 48 are given in FIG. 6.

The packed column described in greater detail in FIG. 6 has a storage container 54, which is connected by means of a flange 58 to a similar flange 59 of the intermixing part 55. Between the two flanges 58, 59 is inserted a plate 60, which has concentrically arranged, openings 61 for the flow of water from the storage container 54 into the intermixing part 55. In the central axis is provided a line 62, which is intended to suck off the air enriched with the gas to be investigated. It passes initially perpendicularly upwards and then horizontally downwards to the outlet for the air. On its bottom it is provided with an inverted funnel 63 for preventing the entry of water into the air line.

The actual intermixing part 55 used for material exchange purposes has on its underside an all-round flange 64, with the aid of which the intermixing part 55 is screwed to the lower part 56 on the flange 65 thereof. Between the two flanges 64, 65 is inserted a support tray 66, which has several openings 67 for through-flow purposes. The support tray 66 receives the packing, which are arranged in the intermixing part 55 up to the line 68 and are indicated by the hatching. The lower part 56 of the packed column also has an all-round flange 69, to which is screwed a bottom 70 provided with the water outlet 49.

The air supplied in counterflow manner passes through the inlet 50 into the lower part 56 of the packed column, being sucked from the storage container by means of the funnel 63, the line 62 and the outlet 51. The water enters the storage container at 47 and from it penetrates the material exchange part through the openings 61. As a result of the flow resistance of the openings 61, a specific water level is obtained in the storage container 54 and can be used for determining the water flow quantity. The water passes downwards through the packing of the intermixing part 55 and it has a relatively large surface. It then drips through the openings 67 of the support tray 66 into the lower part 56 of the material exchange column, from where it is conveyed away via the outlet 49.

The upper portion of the intermixing part 55, i.e. the area above the line 68, is connected with the aid of a pressure compensating line 57 to the portion of the storage container 54 located above the maximum water level. When, as a result of an excessive water flow through the packing, the pressure above the line 68 is greatly reduced, because here air is sucked off by means of 51, this lowered pressure is transferred by means of the pressure compensating line 57 to the storage container 54, so that now a lower pressure acts on the water surface in the storage container 54, so that there is a slowing down of the flow of water through the openings 61. This leads to a self-regulating effect, ensuring that no flooding of the packed column can occur.

In place of cells with a circular cross-section, it is possible to use when determining lower concentrations and in an advantageous manner cells having a rectangular quadrangular, particularly square, or triangular cross-section.

The use of the same optical path for both measurement has the major advantage that divergences during the measurement and reference measurement with respect to the arrangement and formation of the optical path are identical, so that without the use of high precision parts, accurate results can be obtained. The light source is preferably operated with alternating current.

Whilst FIG. 6 shows the packed column and its operation in diagrammatic manner, FIG. 7 is a longitudinal section through an embodiment of the packed column, as can be used in the invention.

As in the embodiment according to FIG. 6, the packed column comprises three parts, namely the upper storage container 54, the middle intermixing part 55 and the lower part 56, which forms a sump for the water flowing through the column. At the interfaces the three parts have in each case a flange 58, 59, 64, 65 with the aid of which the individual parts can be interconnected. The storage container 54 is separated from the middle intermixing part 55 by the plate 60 already mentioned in connection with FIG. 6. The plate 60, which in the embodiment of FIG. 7 is somewhat thicker, contains both the opening 61 for the through-flow of the water and the inverted funnel 63, which is connected by means of a radial bore 71 to the outlet 51. The pressure compensating line 57 is also formed by an axial bore 73, which runs parallel to the opening 61 and on the upper end thereof is mounted a tube 74. The upper end of the tube 74 issues above the water level in the storage container 54.

At the separating point between the intermixing part 55 and the sump 56 a ring plate 75 is inserted between the flanges 64, 65 and has an opening corresponding to the internal diameter of the intermixing part 55.

On the ring plate 75 is provided a wire netting cone as a support body 76 for the packing 77. The cone 78 has an adequate strength, in order to hold the packing 77, as well as a sufficiently large opening to enable water to flow through the packed column. The flanges 58, 59, 64, 65 and the plate 60 or ring plate 75 have coinciding bores passing in the axial direction of the packed column 48 and through which can be passed screws, so that the components can be firmly interconnected.

The internal diameter of the intermixing part 55 is preferably between approximately 5 and approximately 7 cm, particularly approximately 5 cm. The height of the cone 78 roughly corresponds to the internal diameter of the packed column 48 and therefore the diameter of the cone at its base. The height of the portion of the intermixing part 55 covered by the packing 77 is between approximately 40 and 60 cm, particularly approximately 45 cm. The packing can be constituted by glass balls having a diameter of approximately 7 to 8 mm.

In particular by means of a flexible hose, the evaluating apparatus contained in a merely intimated casing 81, is connected to the outlet 51. It more particularly contains all the components necessary for the operation of the apparatus and the evaluation of the results. It is possible to diagrammatically see the cell 18 through which passes the gas flow together with the light source 11 and the sensor 14. By means of a not individually represented evaluating circuit, to the sensor 14 is connected the measuring instrument 34. The casing 81 also contains the pump 52, whose outlet leads to the atmosphere.

In simplified form, the apparatus is operated in such a way that at the air inlet 50 in the sump 56 atmospheric air passes into the lower part. The pump 52 sucks this air through the intermixing part 55 through which flows the water and the space occupied by the packing 77 in the upwards direction, the air having adequate contact with the downwardly flowing water. The air then passes out of the funnel 63, via the bore 71 and the outlet 51 into the evaluating apparatus, which is contained in the casing 81. Although the invention prefers the use of glass balls as packing 77, it is not restricted to the use of balls or the use of glass packing.

FIG. 8 shows in highly diagrammatic form how a comparison measurement can be performed. The medium with the gas to be determined flows through the line 82 into the measuring cell 83. From the latter a line 84 leads to a reaction chamber 85 and from there to the reference cell 86, which is positioned downstream of a suction pump 87.

The reaction chamber 85 contains an inlet 88 for a reaction gas removed from a pressure cylinder 89. Between the pressure cylinder 89 and the inlet 88 there is a pressure gauge 90 and obviously a pressure reducing valve can also be present. Between the inlet 88 and the reaction chamber 85 a diaphragm 92 is located in the casing 91 containing the reaction chamber 85. Thus, this diaphragm 92 separates the reaction gas entering the casing 91 from the pressure cylinder 89 from the actual reaction chamber 85. As a result of the pressure difference the reaction gas diffuses through the diaphragm 92, which leads to a very low gas flow rate. This reaction gas now reacts with the gas, whose concentration is to be measured, so that the medium flowing out of the reaction chamber 85 and into the reference cell 86 no longer contains the gas whose concentration is to be measured. However, it is simultaneously also ensured that no measurement gas passes out into the atmosphere. This is particularly important in those cases where the gas to be measured is prejudicial to the environment. When measuring ozone, for which the invention is particularly suitable, NO is used as the reaction gas.

The flow rate of the medium, in which the concentration is to be measured, is e.g. 30 m h. The inflow rate of the reaction gas is e.g. 0.1 ml/h. Suck flow rates can be achieved with limited cost using the diaphragm 92.

I claim:

1. Apparatus for measuring the concentration of a gas in a liquid medium, comprising:

a radiation source (11,38) and at least one photoreceiver (14) for creating at least one optical path;

at least one measuring cell and at least one optically identical reference cell;

means for alternating the optical path between the measuring cell and the reference cell;

a source of liquid medium with a gas entrained therein;

a source of reference gas; and, an apparatus for exchanging the gas from the liquid medium to a reference gas, said exchange apparatus comprising an upper storage container (54), an intermixing part (55) containing ball packing (77), said storage container (54) being connected to the intermixing part (55) by at least one liquid outlet, said intermixing part (55) having at least one gas outlet (51), at least one liquid outlet (67) communicating with a lower part of the exchange apparatus (56), and a lifting tray for carrying the packing (77), said lower part (56) having an air inlet (50) and a liquid outlet (49), the intermixing part (55) being connected by a pressure compensating line (57) to the storage container (54).

2. The apparatus of claim 1, further comprising a support tray linking the intermixing part (55) with the lower part (56), the lifting tray being positioned over the support tray for carrying the packing (77).

3. The apparatus of claim 1, wherein said pressure compensating line (57) has an opening in the intermixing part (55) above the packing (77), and an opening in the storage container (54) above a maximum liquid level of said storage container.

4. The apparatus of claim 1, wherein the intermixing part (55) has an internal diameter of about 5 cm and a height of about 50 cm, and the height of the packing (77) is about 45 cm.

5. The apparatus of claim 1, wherein the packing (77) rests on a conical wire mesh support body (76), the mesh width of the support body being about 5 mm.

6. The apparatus of claim 1, wherein the packing (77) is made from lead-containing glass, and the surfaces of the balls are polished.

* * * * *